United States Patent
Herman et al.

(10) Patent No.: US 6,228,206 B1
(45) Date of Patent: May 8, 2001

(54) BONDING AGENT COMPOSITION CONTAINING CONDUCTIVE FILLER AND METHOD OF BONDING ELECTRODE TO PRINTED CONDUCTIVE TRACE WITH SAME

(75) Inventors: Daniel F. Herman, Princeton; Vilambi NRK Reddy, Bloomingdale, both of NJ (US)

(73) Assignee: Drug Delivery Technologies, Inc., New York, NY (US)

( * ) Notice: Subject to any disclaimer, the term of this patent is extended or adjusted under 35 U.S.C. 154(b) by 0 days.

(21) Appl. No.: 08/903,048

(22) Filed: Jul. 30, 1997

(51) Int. Cl.[7] ....................................................... B32B 3/12
(52) U.S. Cl. ........................................ 156/306.9; 156/291
(58) Field of Search .................................. 156/291, 292, 156/306.9; 29/843

(56) References Cited

U.S. PATENT DOCUMENTS

| 4,029,628 | * | 6/1977 | Fredberg | 524/361 |
|---|---|---|---|---|
| 4,744,850 | | 5/1988 | Imano et al. | 156/265 |
| 5,095,359 | * | 3/1992 | Tanaka et al. | 257/703 |
| 5,286,417 | * | 2/1994 | Mahmoud et al. | 252/518 |
| 5,296,074 | | 3/1994 | Graham et al. | 156/309 |
| 5,404,637 | * | 4/1995 | Kawakami | 29/843 |
| 5,531,942 | * | 7/1996 | Gilleo et al. | 264/5 |
| 5,605,547 | * | 2/1997 | Lake | 29/25.01 |
| 5,670,826 | * | 9/1997 | Bessho et al. | 257/737 |
| 5,745,985 | | 5/1998 | Ghosh et al. | 29/834 |
| 5,783,867 | | 7/1998 | Belke, Jr. et al. | 257/783 |

* cited by examiner

Primary Examiner—Francis J. Lorin
(74) Attorney, Agent, or Firm—Kirkpatrick & Lockhart LLP

(57) ABSTRACT

The invention relates to a method for using adhesive polymers containing conductive fillers to manufacture iontophoretic devices in which the conductive lead and the conducted printed trace are strongly mechanically bonded together and resulting in electronic interconnection between the conductive lead and conductive printed trace.

7 Claims, 1 Drawing Sheet

BONDING AGENT COMPOSITION CONTAINING CONDUCTIVE FILLER AND METHOD OF BONDING ELECTRODE TO PRINTED CONDUCTIVE TRACE WITH SAME

FIELD OF INVENTION

This invention relates to bonding methods employing adhesive polymers containing conductive fillers to produce electroconductive bonds for use in iontophoretic devices. More specifically, the present invention relates to the utilization of a hot melt polymer containing conductive fillers for the production of an iontophoretic electrode, where the polymer composition has two functions: (a) it provides adhesion between the electrical components and (b) an electronic interconnection between the conductive lead and the conductive printed trace; without the adhesive itself having any conductive properties.

BACKGROUND OF INVENTION

Iontophoretic drug delivery systems, have, in recent years, become an increasingly important means of administering drugs.

Presently there are two types of transdermal drug delivery systems, i.e., passive and iontophoretic. Passive patch systems deliver small and relatively lipophilic drugs through the skin of the patient by diffusion, an example of which would involve the application of a narcotic analgesic patch to provide pain relief. Iontophoresis systems, on the other hand, deliver drug through the skin of the patient through the application of an electromotive force (iontophoresis) to drive ionizable substances (medicament) into the skin so that they can be absorbed by adjacent tissues and blood vessels. Iontophoresis, therefore, allows charged and hydrophilic drugs to be transported across the skin which are poorly deliverable through passive diffusion. Transdermal systems offer advantages clearly not achievable by other modes of administration, such as hypodermic injection which has the associated problem of pain, risk of infection and trauma to the patient. Iontophoresis also has advantages over oral administration in that introduction of the drug through the gastrointestinal tract may result in inactivation of the medicament, food interactions, first pass hepatic metabolism and gastrointestinal side effects.

Conventional iontophoretic devices, such as those described in U.S. Pat. No. 4,820,263 (Spevak, et al.), U.S. Pat. No. 4,927,408 (Haak, et al.) and U.S. Pat. No. 5,084,008 (Phipps), the disclosures of which are hereby incorporated by reference, provide for delivery of a drug or medicament transdermally through iontophoresis. Basically, conventional iontophoretic devices consist of a power source connected to two electrodes, an anode and a cathode, which are individually in ionic contact with an electrolyte or drug reservoir which is in contact with the skin to be treated by the iontophoretic device. When the current is turned on, electrical energy is used to assist in the transport of ionic molecules into the body through the skin, via ionic conduction.

In the recent past, electrically conductive printed traces have been used within an iontophoretic device to make the necessary electrical connections. Conductive adhesives were used for making the electrical connection. The adhesives used for electronic interconnection bonding known in the art prior to the present invention, was comprised of epoxy and pressure sensitive adhesives. The starting points for making epoxy adhesives are fluid viscous low molecular prepolymer materials obtained either as single component or two component compositions. In the prior art where a conductive additive filler is used, the filler must be incorporated before curing occurs. The additiion of a conductive filler will increase the viscosity of the prepolymer and if the filler concentration is too high, the epoxy prepolymer-filler mix will be difficult if not impossible to apply. Therefore the selection of the filler is limited to the most highly conducting and coincidentally, the expensive materials, e.g. silver powder, and even thenit may not be possible to incorporate sufficient conducting filler to accomplish its purpose. Once the conductive filler epoxy is formed and cured, the epoxy is irreversibly cured and is cannot be used in remelting and resealing operations. It is incapable of bonding to a new surface and therefore could not be used in assembly of a device with the conductive adhesive in dry form mostly because once dried or cured it cannot be remelted or recured. Further disadvantages of epoxies in addition to the high cost, are slow curing time, toxcity of the prepolymers and possible vapor release or outgassing during curing, they could not be used in high speed manufacturing due to long cure times and due to their liquid form there were problems with using conventional coating techniques.

Pressure sensitive adhesives are applied in thin layers which produce weak bonds especially when attempting to bond to a metal mesh. Costs are high and efficiency of the conductive component is low resulting in poor electrical conductivity. Prior art pressure sensitive adhesives also had other manufacturing and application problems. For example, due to the tendency of pressure sensitive adhesives to retain solvent they resulted in outgassing during preparation and use.

These difficulties and shortcomings have led Applicants to the present invention which overcomes these difficulties and shortcomings.

SUMMARY OF THE INVENTION

The invention relates to bonding methods employing adhesive polymers to produce electronic interconnection and strong mechanical bonding for use in iontophoretic devices. More specifically, the present invention relates to the utilization of a hot melt adhesive plastic, free of polymer solvents and containing conductive fillers for the production of an iontophoretic electrode, where the polymer composition has two functions: (a) it provides adhesion between the external conducting electrical lead and the iontophoretic electrode-containing reservoir structure and (b) establishes an electronic interconnection between the two; without the adhesive polymer itself being conductive.

An object of the present invention is to provide a composition capable of instantly mechanically bonding the external electrode lead of an iontophoretic device to a conductive printed trace and maintaining a good electrical connection therewith.

Another object of the present invention is to provide a composition capable of instantly forming both a mechanical and electrical bond with a conductive printed trace using conventional coating or dispensing technologies.

Another object of the present invention is to provide a thermoplastic polymer composition free of solvents and containing conductive fillers which composition is capable of being melted to a molten state and applied and cooled to produce a spotted zone of a dry solidified polymer of controlled weight and size on to either the electrode or the conductive printed trace prior to assembly.

Another object of the present invention is to provide a composition which has no problems with outgassing.

Another object of the present invention is to provide a composition which uses low pressure and low temperature processing.

Another object of the present invention is to provide a composition which results in high speed formation of bonds.

Another object of the present invention is to provide a composition which can be used in the assembly steps in a variety of forms which can be repeatedly melted and resolidified.

Another object of the present invention is to provide a composition for low cost processing.

DETAILED DESCRIPTION

Figure 1:
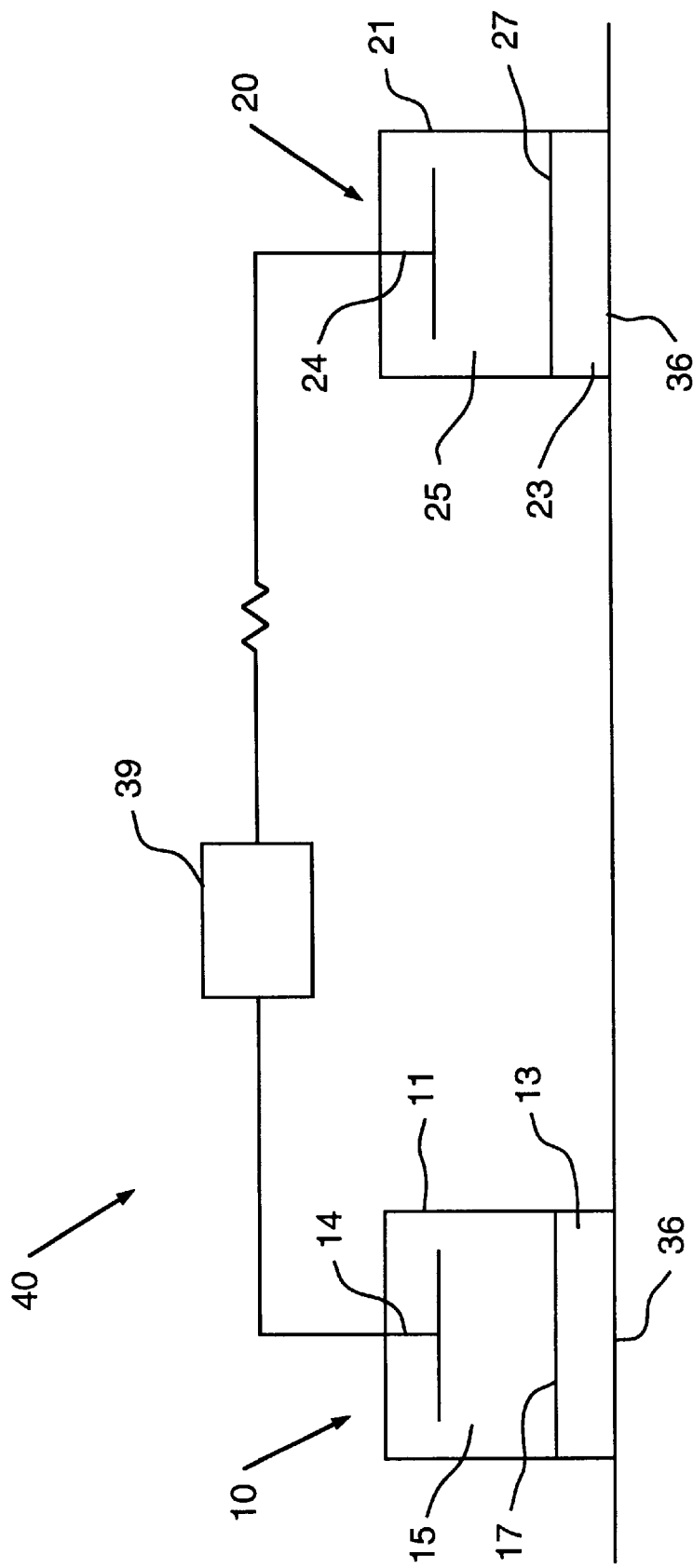
FIG. 1 depicts an embodiment of the device of the present invention.

The present invention relates to a novel method and composition for forming a bond between a conductive metal lead and a conductive printed trace in an iontophoretic drug delivery system. The invention is based on the concept of selecting a thermoplastic adhesive polymer which exhibits high flow under the conditions used for sealing the conductive lead to the conductive printed trace and add conductive fillers to that polymer prior to forming the seal.

The conductive fillers may be by way of example and not limitation, vanadium, platinum, palladium, chromium, magnesuim, palladium, nickel, carbon black, graphite, aluminum, titanium, silver, copper, conductive organic polymers and mixtures thereof. The conductive lead can be a metal mesh, woven wire, metallic ribbon, expanded foils or the like. Also it is anticipated by the present invention that the metallic materials may have a raised or depressed surface or surface portion which would permit direct contact between the conductive lead and the conductive printed trace and provide surfaces on both sides for the thermoplastic polymer composition to adhere to each. Under the mild pressure and temperature conditions used to make the seal, the adhesive polymer composition flows readily, allowing the portions of the conductive lead and the conductive trace to mechanically and electronically interconnect. Once the conductive lead and printed trace are pressed into direct contact, the resulting bond has low electric resistance and forms a good mechanical bond. Concurrently the adhesive polymer is also in direct contact with areas of the printed trace which are not touched by the strands of the open metal mesh and are therefore exposed to the composition. Sufficient adhesive polymer composition is used so that it will fill the pores of the open mesh and also adhere to the sides and even the top surfaces of the strands when the seal is made.

The adhesive polymer composition thus performs the following functions: (a) it seals the metal mesh into a position which is in direct contact with the conductive trace, (b) it adheres strongly to the trace and (c) it bonds strongly to the metal lead or mesh and establishes an electrically conductive pathway between the conductive printed trace and the conductive lead. The final effect is to produce a physically strong bond having good electrical conductivity which is unaffected by mechanical stress.

A particular advantage is that the composition is heat resealable, the composition can be repeatedly melted and solidified. However, it should be noted that at high concentrations of conductive filler the melt viscosity of the loaded prepolymer will increase to the point where flow is severely impaired and heat resealability will be lost. Since the effect on viscosity is dependent upon the volume fraction of the conductive filler vs. the total volume of the film, therefore, the density of the conductive filler directly effects the conductive filler concentration which is optimal. Logically lower density conductive fillers such as carbon black or graphite, a high volume fraction is easily reached at lower weight concentrations (as opposed to a high density conductive filler such as silver). The advantage of using a lower density conductive filler is that conductivity which is based on the degree of particle to particle contact within the filler-prepolymer mixture and conductivity can be reached at lower loading and cost.

The adhesive hot melt polymer composition can be applied in a variety of different forms: (a) as a water based or an inert organic dispersion of microscopic polymer and conductive filler particles, (b) as fine particle size polymer and conductive filler powders used for use in air laying equipment, (c) in the form of conductive filler containing polymer sticks, chips, powders which are melted then applied in a liquified form with standard hot melt, extrusion or hot melt screen coating equipment, or (d) as a molten conductive filler containing polymer fluid which can be applied as individual drops of desired thickness or by dipping.

Useful hot melt polymers which are uncrosslinked, linear or branched polymers include, but are not limited to, the polyamides, the polyesters, acrylics, cellulosics, polyethers, vinylchloride, and a copolymer of ethylene/vinyl acetate (EVA) or mixtures thereof. Particularly useful polymers are those which will melt and exhibit high flow at temperatures in the range of from about 200° to about 370° F. and rapidly solidifies. By way of example and not limitation, are EVA polymers which have low melt viscosities in the range of from about 1000 to about 2000 centipoise (cps) within the temperature range cited.

Using standard commercial equipment such polymers can be readily delivered as discrete molten drops in patterns designed to conform with the requirements of the electrode. In an initial step, the polymer drops can be applied either to a continuous roll of the metal mesh or the printed conducting trace. Preferably, at this point, the drops would be flattened to a desired thickness depending upon the thickness and size of the openings of the conductive mesh. Once applied the polymer will solidify rapidly and the roll can be used immediately in the next step of the manufacture or it can be wound and stored for future processing. An important and critical property of these polymers is that they can be repeatedly melted and solidified. Therefore the polymer deposition step can be carried out in an off-machine operation and the polymer coated mesh or printed trace can then be used in a subsequent operation to produce the final iontophoretic electrode. Thus, either the mesh or the printed trace, spotted with a pattern of discrete solidified polymer droplets containing conductive fillers, can be assembled with its opposing members and the manufacturing completed by re-heating and re-melting the droplet and pressing the printed trace and the conductive lead together to form the desired structure joined by a polymer bond containing conductive fillers between the conductive printed trace and the conductive lead. In the alternative, the two steps can also be carried out sequentially without interruption between polymer deposition and final bonding.

When the adhesive polymer is employed in the form of an aqueous or inert organic slurry of polymer particles, it is applied to the trace by means of a coating or printing screen which is capable of depositing controlled amounts of material in a patterned form. Screens delivering from about 25 to about 250 cm³ of slurry per square meter of the trace surface are most useful. The deposited polymer is then dried and prefused and in an off machine operation. The treated trace is finally assembled with the metal mesh and the two are fused together to complete the operation.

Taking into account the conductive mesh size, one of ordinary skill can choose the screen thickness and the diameter and spacing of the holes necessary, to vary the polymer deposit, in either a continuous coating or a pattern of individual spots of polymer. Either type will produce strong bonds of good conductivity. A continuous coating is produced by thicker screens with large diameter, closely spaced holes, particularly when the viscosity of the printing paste is low. With higher viscosity pastes and more widely spaced holes, individual spots of polymer will be deposited, the pattern depending upon screen design.

In the case of continuous coatings, the heat and pressure applied during the bonding step will still result in low electrical resistance since the polymer flows sufficiently to allow the conductive lead, i.e., the metal mesh, to be forced into direct contact with the conductive printed trace and become bound in place after cooling. When a coating of discrete spots of polymer is deposited, contact between the metal mesh and the trace occurs readily in the uncoated regions between the spotted polymer, resulting in low resistance. Strong bonding is obtained by having a sufficient amount of polymer laid down in the spotted regions resulting in anchoring of the conductive lead to the conductive (printed) trace.

Preferably, to ensure strong mechanical bond, the polymer when applied should be applied to surface areas beyond the electronic interconnection, most preferably on to the substrate backing on to which the conductive trace has been printed. Additionally, when greater mechanical strength is required, a fast drying adhesive (i.e. Duco™), or a fast curing U.V. curable coating is coated over the electrode already bound to the conductive trace and the assembly is exposed to U.V. radiation.

When the polymer is used in a powdered form, it may be applied to the printed trace with commercially available powder deposition equipment. The deposited powder is then compacted and sealed in place by heating to its softening point and final assembly into an iontophoretic electrode is carried out as before.

An embodiment of the present invention provides for a method of mechanically connecting an electrically conductive lead to an electrically conductive printed trace which mechanical connection results in electronic interconnection between the conductive lead and conductive printed trace, which involves the following steps:

(a) depositing a thermoplastic polymer composition containing conductive fillers between the printed trace and the conductive lead, (b) applying heat and pressure to the thermoplastic polymer composition to melt the thermoplastic polymer composition causing it to adhere to the lead and the printed trace, while concurrently bringing the printed trace and conductive lead into direct electrical contact and (c) cooling the thermoplastic polymer composition to place the conductive lead and the printed trace in electrical communication.

The method of the present invention may alternatively be performed such that step (a) further includes the sub-steps of:

heating the deposited thermoplastic polymer composition to first melt the thermoplastic polymer composition on to the lead, cooling the thermoplastic polymer composition, and placing the thermoplastic polymer composition between the lead and the printed trace.

Another alternative with respect to the method of the present invention would be one in which step (a) as originally described above would further include the sub-steps of:

heating the deposited thermoplastic polymer composition to first melt the thermoplastic polymer composition containing conductive fillers on to the printed trace, cooling the thermoplastic polymer composition, and placing the thermoplastic polymer composition between the lead and the printed trace.

Another embodiment of the present invention provides for an electrode assembly. The electrode assembly has a current distributing member having an electrically conductive lead which is mechanically connected to an electronically conductive printed trace through a thermoplastic polymer bond containing conductive fillers which results in an electronic interconnection between the conductive lead and conductive printed trace.

Another embodiment of the present invention provides for an iontophoretic device for delivery of a drug to a patient. The iontophoretic device has (a) a current distributing member having an electrically conductive lead which is mechanically connected to an electronically conductive printed trace through a thermoplastic polymer bond containing conductive fillers which results in an electronic interconnection between the conductive lead and conductive printed trace;

(b) an ionized substance reservoir containing an ionized or ionizable substance, in electrical communication with the current distributing member and adapted to be placed in ionic communication with the epithelial surface of a subject;

(c) an electrolyte reservoir containing an electrolyte, in electrical communication with an indifferent electrode and in ionic communication with the epithelial surface;

(d) an electrical power source in current delivering connection with the current distribution member and the electrolyte reservoir.

The iontophoretic device of the present invention may by way of example and not limitation include the following component and materials.

A. The Current Distributing Member (Active Electrode)

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes current without being eroded or depleted due to the distribution of current, and conducts current through the generating ions by either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

Additional types of materials useful as current distributing members according to the invention are disclosed in detail in a co-pending application entitled Low-Cost Electrodes for an Iontophoretic Device, by V. Reddy et al., Ser. No. 08/536,029, filed on Sep. 29, 1995, the disclosure of which is incorporated by reference herein.

The current distributing member may take any form known in the art, such as the form of a plate, foil layer, screen, wire, or dispersion of conductive particles embedded in a conductive matrix.

B. The Electrolyte Reservoir

1. Electrolytes

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to supply ions for conducting current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having a concentration of less than 1 mole/liter (<1 M), more preferably at about physiological concentration. Other electrolytes include salts of physiological ions including, but not limited to, potassium ($K^+$), chloride ($Cl^-$), and phosphate ($PO_4^-$). The salt and its concentration may be selected as desired for particular applications. Other species may be selected by the skilled artisan for inclusion in the electrolyte reservoir. Such other reservoir species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays, polyoxyethylenes), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. The Ionized Substance (Drug) Reservoir

The reservoir structure of the iontophoretic apparatus of the invention further includes an ionized substance reservoir. The ionized substance reservoir must be in ionic communication with an epithelial surface.

The construction of the ionized substance reservoir must be consistent with the requirements for ionic communication with the epithelial surface and electrical communication with the current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. In preferred embodiments, a cross-linked hydrogel in the electrolyte reservoir, because it inherently contains significant amounts of water, can serve as a water reservoir during iontophoresis.

It may be desirable to provide the solution of active ingredient with a buffer. The ion of the buffer of like charge to the drug ion should have low ionic mobility. The limiting ionic mobility of this ion is preferably no greater that $1 \times 10^{-4}$ cm$^2$/volt-sec.

Calcium ions have a strong affinity for certain drugs, i.e., bisphosphonates and, therefore, formulation steps must be taken to avoid interaction of the drug and residual amounts of calcium in the reservoir. This may be achieved by the addition of agents capable of chelating calcium such as citrate salts, EDTA and other like chemicals.

D. The Ionizable Substance (Drug) for Iontophoretic Delivery

An ionic drug can be delivered from either the anode, the cathode, or both simultaneously. For example, if the ionic substance to be driven into the body is positively charged, then the positive electrode or anode will be the active electrode and the negative electrode or cathode will serve to complete the electrochemical circuit. Alternatively, if the ionic substance to be delivered is negatively charged, then the negative electrode will be the active electrode and the positive electrode will be the indifferent electrode. Since all bisphosphonates usually possess an overall negative charge at skin pH, the preferred embodiments of the present invention are directed to ionic drugs driven from the cathode of the iontophoretic device. However, it is to be understood that an anodic configuration may be used to drive positively charged chemical modifications of the drug to be delivered without departing from the spirit of the invention.

It is believed that this invention has utility in connection with the delivery of active ingredients within the broad class of bisphosphonates as well as chemical modifications of bisphosphonates.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized substance reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit. Various types of electrodes may be employed such as is described in United States application entitled Low-Cost Electrodes for an Iontophoretic Device, by Reddy et al., Ser. No. 08/536,029 filed Sep. 29, 1995.

As depicted in FIG. 1 an embodiment of the iontophoretic device of this invention 40 is configured as follows:
an anode patch 10, having an anode electrode compartment 11 in ionic communication with a skin contacting compartment 13. The skin contacting compartment 13 and the anode electrode compartment 11 maybe separated by a compartment separation means (membrane) 17. The anode electrode compartment 11 also contains an anode 14 and an electrolyte (anolyte) 15. The skin contacting compartment is attached to the patient's skin 36. A cathode patch 20, having a cathode electrode compartment 21 in ionic communication with a skin contacting compartment 23. The skin contacting compartment 23 and the cathode electrode compartment 21 maybe separated by a compartment separation means (membrane) 27. The cathode electrode compartment 21 also contains an cathode 24 and an electrolyte (catholyte) 25. The skin contacting compartment is attached to the patient's skin 36.

The following examples are presented to explain and exemplify the embodiments of the present invention and are not intended to limit the scope of the present invention.

EXAMPLES

Example 1

10 pts of a 25% suspension of 2.5 micron graphite particles in water (Dixon Ticonderoga GW425) was mixed with 2 pts of a linear polyamide powder (Bostik #5216A, a Nylon copolymer melting at 153 C) and the slurry was spotted on a printed silver trace. The deposited slurry was dried to give a spotted region containing 52.4% graphite and 47.6% polyamide. An aluminum mesh lead was then laid over the deposit and heated under mild pressure to 130–155 C for 5 seconds. A strong laminate was formed between the printed trace and aluminum mesh lead and conductivity of the seal was found to be high.

Example 2

The above experiment was repeated using 10 pts of the graphite suspension with 4 pts of the polyamide powder to give a spotted region with a 35.5/64.50 graphite/polyamide ratio. Adherence was excellent and resistance was less than 1 ohm. The experiment was repeated substituting a suspension of carbon black powder Vulcan XC72 (Cabot) in place of the graphite with similar results. Black Pearls (Cabot) also performed similarly.

Example 3

Slurries of both a polyester and a polyamide to which was added the graphite suspension of Ex. 1 were tested individually and strong bonds and very low resistivity were obtained. The polyamide slurry (EMS Corp. #2120-1) contained 30% polyamide in suspension. The polyester slurry (EMS Corp. #2120-1) had the same concentration. Ratio of graphite/polymer was 35/65.

Example 4

Using the polyamide suspension, $2120-1, Ex. 3 was repeated substituting a fine silver powder for graphite. The weight ratios of silver/polyamide employed were 30/70 and 40/60. The slurry was applied through a printing screen and dried and fused at 300 F. The mesh was bonded to the trace as before and high bond strength was obtained. Resistivity was low.

Example 5

A low melting ethylene-vinyl acetate copolymer (Evans Adhesive Co. #07460) melting at 200 F with a melt viscosity of 800 cps@375 F was employed as the adhesive binder. The copolymer was melted and silver powder was added with agitation to yield a slurry containing a 30% concentration of silver. The molten slurry was then applied to a printed trace using a hot melt gun to deliver ⅛ to ¼" diameter spots at selected points on the trace. Seals were then made between the spotted regions and strips of a conducting aluminum mesh in the manner described before. Strong adhesion and low resistivity were obtained. Similar results were obtained with a 40% concentration of silver powder.

We claim:

1. A method of mechanically connecting an electrically conductive lead to an electrically conductive printed trace for the formation of an iontophoretic electrode which mechanical connection results in electronic interconnection between the conductive lead and conductive printed trace of an iontophoretic-electrode containing structure comprising the steps of:

a) selecting a thermoplastic polymer composition containing electrically conductive fillers;

b) depositing said thermoplastic polymer composition containing said electrically conductive fillers between a printed trace of an iontophoretic-electrode containing structure and a conductive lead;

c) applying heat and pressure to the thermoplastic polymer composition to melt the thermoplastic composition causing it to adhere to the lead and the printed trace of the iontophoretic-electrode containing structure, while concurrently bringing the printed trace and conductive lead into direct electrical contact; and d) cooling the thermoplastic polymer composition to place the conductive lead and the printed trace in electrical communication thereby forming the iontophoretic electrode.

2. The method of claim 1 wherein said selecting step further comprises selecting the thermoplastic polymer from the group consisting of: polyamides, polyesters, ethylene vinyl acetate, acrylics cellulosics, and mixtures thereof.

3. The method of claim 1 further including providing the conductive lead selected from the group consisting of metal mesh, woven wire and mixtures thereof.

4. The method of claim 3 wherein the thermoplastic polymers containing conductive fillers further comprises selecting the fillers in the form from the group consisting of: fine particle powder, polymer sticks, polymer chips, flakes, molten polymer, aqueous or inert organic based dispersion slurry of polymer particles containing conductive fillers and mixtures thereof.

5. The method of claim 1 further comprising selecting the conductive fillers from the group consisting of carbon black, graphite, silver, copper and mixtures thereof.

6. The method of claim 1 wherein said depositing step further includes the sub-steps of:

heating the deposited thermoplastic polymer composition to first melt the thermoplastic polymer composition onto the lead;

cooling the thermoplastic polymer composition; and placing the thermoplastic polymer composition between the lead and the printed trace.

7. The method of claim 1 wherein said depositing step further includes the sub-steps of:

heating the deposited thermoplastic polymer composition to first melt the thermoplastic polymer composition containing conductive fillers onto the printed trace;

cooling the thermoplastic polymer composition; and placing the thermoplastic polymer composition between the lead and the printed trace.

* * * * *

UNITED STATES PATENT AND TRADEMARK OFFICE
CERTIFICATE OF CORRECTION

PATENT NO. : 6,228,206 B1
DATED : May 8, 2001
INVENTOR(S) : Herman et al.

Page 1 of 1

It is certified that error appears in the above-identified patent and that said Letters Patent is hereby corrected as shown below:

Column 2,
Line 13, after "and", delete "is".

Column 3,
Line 30, after "magnesium", delete "palladium".

Column 9,
Line 56, after "may", insert -- be --.

Column 10,
Line 66, after delete "$" and replace therewith -- # --.

Signed and Sealed this

Sixteenth Day of April, 2002

Attest:

JAMES E. ROGAN
Director of the United States Patent and Trademark Office

Attesting Officer